United States Patent [19]
Amos

[11] Patent Number: 4,970,356
[45] Date of Patent: Nov. 13, 1990

[54] RAINFALL RESPONSIVE SWITCH CONSTRUCTION

[76] Inventor: Gary T. Amos, 413 West Ave., Northvale, N.J. 07647

[21] Appl. No.: 539,199

[22] Filed: Jun. 18, 1990

[51] Int. Cl.$^5$ .......................................... H01H 29/00
[52] U.S. Cl. ............................... 200/61.05; 200/61.04; 200/DIG. 14
[58] Field of Search ............... 200/61.04, 61.05, 61.06, 200/61.07, 61.2, DIG. 41, DIG. 40, DIG. 14; 307/118; 340/601, 602

[56] References Cited

U.S. PATENT DOCUMENTS

| | | | |
|---|---|---|---|
| 1,280,116 | 9/1918 | Troiano | 200/61.04 X |
| 2,369,215 | 2/1945 | Crise | 200/61.07 |
| 2,668,202 | 2/1954 | Kaplan | 200/61.05 |
| 2,769,872 | 11/1956 | Clark | 200/61.05 |
| 2,787,695 | 4/1957 | Dyke | 200/61.05 X |
| 3,127,485 | 3/1964 | Vitolo | 200/61.05 |
| 3,157,800 | 11/1964 | Burwell | 200/61.05 X |
| 3,210,492 | 10/1965 | Hayes | 200/61.04 |
| 3,440,396 | 4/1969 | Greene, Jr. | 200/61.04 X |
| 3,500,844 | 3/1970 | Sanner | 200/61.05 X |
| 3,562,731 | 2/1971 | Hsu | 200/61.04 X |
| 3,657,498 | 4/1972 | Heindorff | 200/61.04 |
| 3,808,385 | 4/1974 | Klinefilter | 200/61.04 |
| 4,015,616 | 4/1977 | Hanff | 200/61.04 X |
| 4,246,575 | 1/1981 | Purtell et al. | 200/61.04 X |
| 4,598,273 | 7/1986 | Bryan et al. | 200/61.04 X |
| 4,598,333 | 7/1986 | Adams et al. | 200/61.04 X |

*Primary Examiner*—J. R. Scott
*Attorney, Agent, or Firm*—Samuelson & Jacob

[57] ABSTRACT

A rain water sensitive switch construction for use in connection with a lawn sprinkling system includes a pair of horizontally oriented perforated electrical contact plates spaced apart vertically to establish an air gap between the spaced apart contact plates, and a housing within which the contact plates are mounted above ground so that rain water passes into the housing and through the contact plates to bridge the gap and effect electrical contact between the contact plates immediately upon the onset of rain and is not retained between the plates so that electrical contact between the contact plates is discontinued immediately when the rain stops.

11 Claims, 2 Drawing Sheets

RAINFALL RESPONSIVE SWITCH CONSTRUCTION

BACKGROUND OF THE INVENTION

The present invention relates generally to irrigation systems and pertains, more specifically, to a rainfall responsive switch for discontinuing the supply of water in an irrigation system, such as a lawn sprinkling system, in response to the occurrence of rain at the irrigated area in order to conserve water and the energy employed to deliver the water to the irrigated area, as well as to prevent over-watering.

Irrigation systems of the type designed for watering lawns are in common use. It has been suggested that electronic controls be employed in such systems for discontinuing the sprinkling of water during periods of rain to thereby conserve water and energy, and to prevent over-watering. Thus, several patents to Sanner, namely, U.S. Pat. Nos. 3,500,844, 3,848,616, 3,915,185, 4,014,359 and 4,246,574, illustrate and describe a variety of control arrangements in which rain responsive switches are incorporated into control circuits for lawn sprinkler systems. While many of these rain responsive switches rely upon moisture absorption to effect operation, some of the above-enumerated patents recognize that instant switch activation and deactivation can be advantageous when combined with electronic circuit devices for better control, and disclose a planimetric switch designed for such instant response.

The present invention provides an improvement in the construction of a rainfall responsive switch of the type which is activated immediately upon the occurrence of rain and is deactivated when rainfall stops. As such, the present invention provides an improved switch construction which attains several objects and advantages, some of which may be summarized as follows: Enables rain water to pass through without substantial accumulation for immediate activation upon the onset of rain and deactivation as soon as the rain stops; allows ambient air to pass through, not only for venting to restore the switch to a deactivated state quickly, but for enabling an omnidirectional flow of air to remove any loose airborne debris which otherwise could impede such deactivation; provides a construction which is highly sensitive to rainfall and remains sensitive over longer service periods without the requirement for frequent maintenance and cleaning to attain long-term sensitivity; exhibits a construction which tends to maintain itself in working order, thereby reducing cleaning and maintenance requirements for long-term reliability; and provides a rugged construction which withstands exposure to ambient conditions for reliable operation over a long service life.

OBJECTS OF THE INVENTION

The above objects and advantages, as well as further objects and advantages, are attained by the present invention which may be described briefly as a rain water sensitive switch construction for use in connection with irrigation means, such as a lawn sprinkler system, the rain water sensitive switch construction comprising: a housing having a top and a bottom for installation above ground with the top facing vertically upwardly and the bottom facing vertically downwardly, the top and bottom including openings for allowing rain water to enter the housing and for precluding entry of airborne debris into the housing while enabling relatively free circulation of ambient air through the housing; first and second electrical contact plates within the housing, between the top and the bottom, the contact plates being juxtaposed with one another such that the first contact plate overlies the second contact plate with the contact plates spaced apart vertically in close proximity to one another to establish an air gap between the contact plates; and perforations in the first and second contact plates for enabling rain water to pass through the perforations and bridge the gap between the plates as the rain water passes through the perforations, and to enable relatively free circulation of ambient air through the contact plates.

BRIEF DESCRIPTION OF THE DRAWINGS

The invention will be understood more fully, while still further objects and advantages will become apparent, in the following detailed description of a preferred embodiment of the invention illustrated in the accompanying drawing, in which.

DETAILED DESCRIPTION

Figure 1:
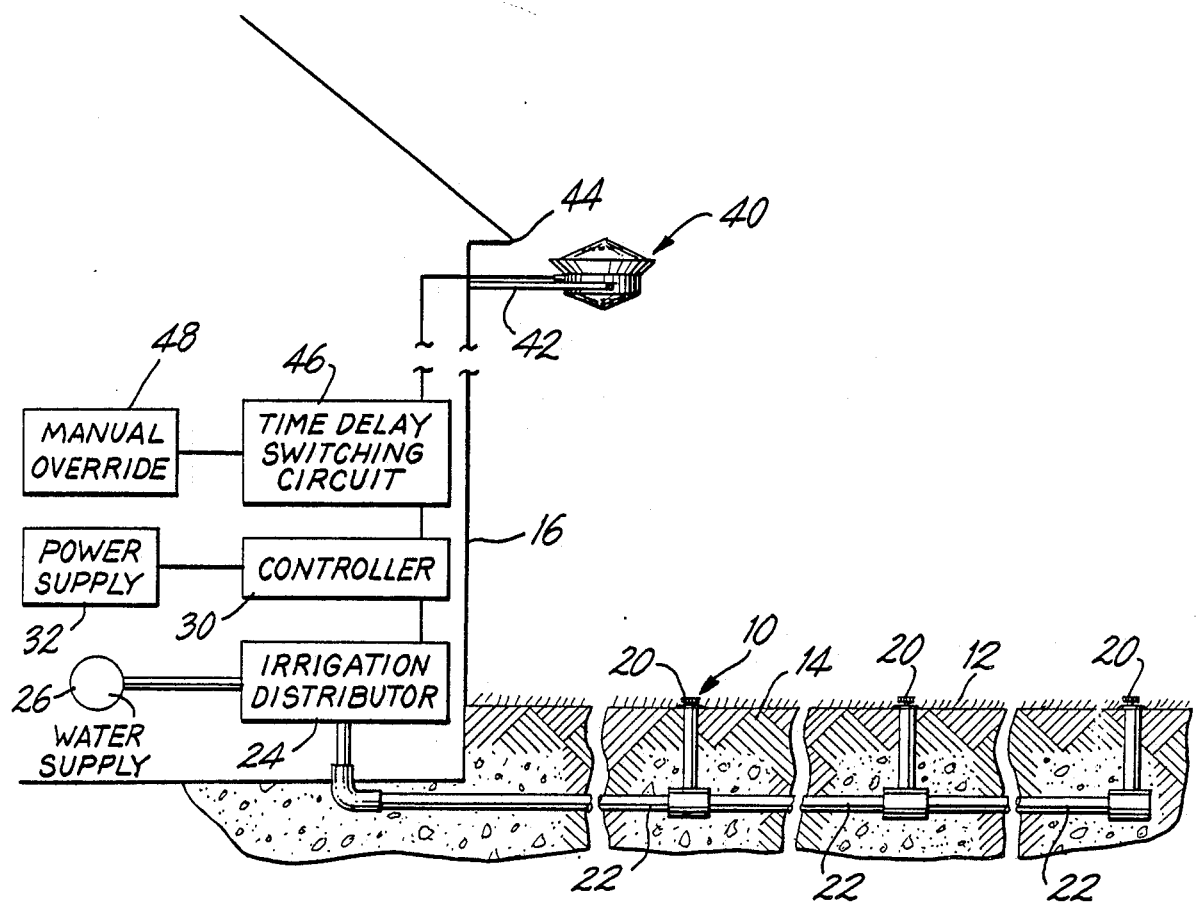
FIG. 1 is a generally schematic diagram of a lawn sprinkling system employing a rainfall responsive switch constructed in accordance with the present invention.

Referring now to the drawing, and especially to FIG. 1 thereof, irrigation means is shown in the form of a lawn sprinkling system 10 installed for sprinkling water upon a lawn 12 which extends along the ground 14 outside a building 16. Lawn sprinkling system 10 includes a plurality of sprinklers 20 embedded in the ground 14 and connected to distribution pipes 22 which, in turn, are connected to an irrigation distributor 24, preferably placed within the building 16. Irrigation distributor 24 comprises a valve arrangement for controlling the flow of water from a water supply 26 to the distribution pipes 22 and, consequently, to the sprinklers 20. A controller 30 is connected electrically to an electric power supply 32 and includes electronic controls for controlling the operation of the irrigation distributor 24 so that water is supplied to the lawn 12, through the sprinklers 20, periodically, at intervals and durations determined by a selected program set into the controller 30, all in a manner now well known in the art of lawn sprinkler systems.

A rain water sensitive switch 40 is mounted upon a bracket 42 affixed to the building 16 in such a way as to assure that the switch 40 is exposed to the ambient conditions above the lawn 12. Thus, bracket 42 is long enough to locate the switch 40 beyond any overhanging structure, such as the eaves 44 of building 16, and is placed above ground 14 and far enough away from the lawn 12 to assure that the switch 40 is unaffected by the operation of the sprinklers 20 of lawn sprinkling system 10. Upon the onset of rain, switch 40 will be activated to operate a time delay switching circuit 46 which, in turn, interrupts the regular program set into the controller 30 to shut down any sprinkling of lawn 12 by the lawn sprinkling system 10 for a predetermined timed interval. A preferred predetermined timed interval is eight hours; however, other intervals may be selected depending upon the climate in the vicinity where the lawn sprinkling system 10 is installed. Upon expiration of the predetermined timed interval, if the switch 40 indicates that the rain has stopped, the controller 30 will be free to resume its regular program of operation. If, upon expiration of the predetermined timed interval, the switch 40 indicates that the rain is continuing, the controller 30 will continue to maintain the lawn sprinkling system 10 shut down. In this manner, the lawn sprinkling system 10 is made responsive to rainfall for the conservation of water, and the energy needed to deliver the water through the sprinklers 20 to the lawn 12, as well as for the prevention of overwatering. A manual override 48 enables selective operation of the controller 30 independent of the condition of the switch 40 and the time delay switching circuit 46. For reasons of safety, convenience, and ease of installation and maintenance, as well as for protection against the elements of weather and climate, most of the control components of the lawn sprinkling system 10 are located inside the building 16, with only the switch 40 placed outside for exposure to ambient conditions.

Turning now to FIGS. 2 through 5, switch 40 includes a housing 50 having a generally annular sidewall member 52, a top member 54 facing vertically upwardly and a bottom member 56 facing vertically downwardly. Each of the members 52, 54 and 56 preferably is molded of a polymeric material having requisite strength and durability for service under the conditions to be described below. Sidewall member 52 has a generally cylindrical portion 60 and an integral funnel-like, frusto-conical portion 62 extending vertically upwardly and radially outwardly from the cylindrical portion 60. Top member 54 has an outer surface configuration which is upwardly convex, the preferred configuration being generally conical, with an uppermost apex 64 at the center of the top member 54 and a generally circular lowermost rim 66. A plurality of apertures 68 in the top member 54 are located along a circle and establish openings through the top member 54, for purposes which will be set forth in detail below. A plurality of notches 70 are spaced along the rim 66 and establish further openings through the top member 54 and radial fingers 72 between the notches 70. The radial fingers 72 are resiliently deflectable and are received within an annular groove 74 in the frusto-conical portion 62 of the sidewall member 52 to secure the top member 54 assembled with the sidewall member 52. The top member 54 is selectively disassembled from the sidewall member 52 and assembled with the sidewall member 52 by resiliently snapping the radial fingers 72 out of or into the groove 74. Such ease of assembly and disassembly of the top member 54 and the sidewall member 52 facilitates access to the interior of the housing 50 for periodic cleaning and maintenance. The bottom member 56 is downwardly concave, the preferred configuration including an upper cylindrical portion 76 and an integral lower conical portion 78 with a lowermost point 80. A plurality of apertures 82 in the cylindrical portion 76 and a plurality of apertures 84 in the conical portion 78 establish openings through the bottom member 56 for purposes to be described in detail below. A threaded connection at 86 enables selective assembly and disassembly of the bottom member 56 and the sidewall member 52.

Switch 40 includes electrical contact means in the form of a first electrical contact plate 90 and a second electrical contact plate 92, both electrical contact plates 90 and 92 being placed within the interior of the housing 50 in juxtaposition with one another such that the first contact plate 90 overlies the second contact plate 92 with the contact plates 90 and 92 spaced apart vertically in close proximity to one another to establish an air gap 94 between the first and second contact plates 90 and 92. The contact plates 90 and 92 preferably are essentially planar and are maintained parallel to one another so that the gap 94 is uniform throughout the extent of the contact plates 90 and 92. Perforations 96 in each of the contact plates 90 and 92 provide openings through the contact plates 90 and 92. The contact plates 90 and 92 preferably are constructed of a corrosion resistant electrically conductive material, such as stainless steel.

Figure 4:
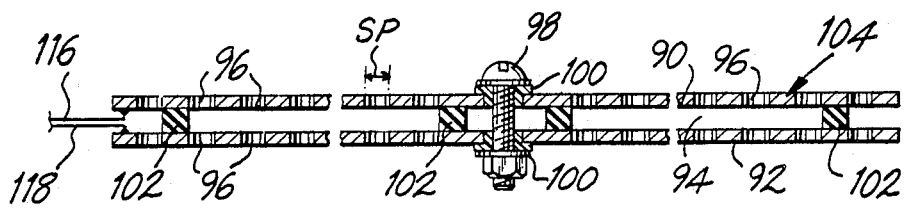
FIG. 4 is a diametric cross-sectional view of a subassembly of the switch.
Figure 5:
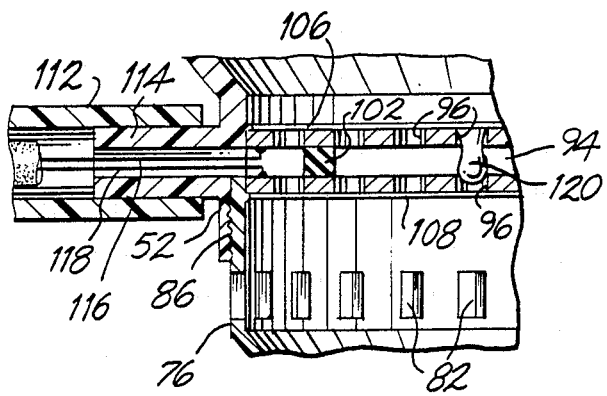
FIG. 5 is a still further enlarged fragmentary cross-sectional view of a portion of FIG. 3.

As best seen in FIG. 4, in the illustrated construction, the contact plates 90 and 92 are secured together by a central threaded fastener 98 which is electrically isolated from the contact plates 90 and 92 by insulating grommets 100. Spacers 102 of electrically insulating material maintain the gap 94 between the contact plates 90 and 92 and complete a contact sub-assembly 104 within which the contact plates 90 and 92 are affixed, together with the spacers 102. As best seen in FIG. 5, the contact sub-assembly 104 is secured within the interior of the housing 50, intermediate the top member 54 and the bottom member 56, between an upper rib 106 molded unitary with the cylindrical portion 60 of the sidewall member 52 and a lower rib 108 molded unitary with cylindrical portion 76 of the bottom member 56, with a clamping force established between the confronting ribs 106 and 108 by the threaded connection at 86. An electrical cable 110 carries a connector sleeve 112 which fits over a connector nipple 114 on the sidewall member 52 to secure the cable 110 to the housing 50. Cable 110 includes a pair of conductors in the form of a first electrical wire 116 connected to the first contact plate 90 and a second electrical wire 118 connected to the second contact plate 92. The conductors of the cable 110 are connected to the time delay switching circuit 46.

During ordinary operation of the lawn sprinkling system 10, the controller 30 operates the irrigation distributor 24 in accordance with a prescribed program to alternately open communication between the water supply 26 and the sprinklers 20 and close such communication for predetermined periods. Should rain occur during a sprinkling cycle, rain water will enter the housing 50 of switch 40, through the openings established by apertures 68 in the top member 54 of the housing 50, and reach the contact sub-assembly 104. As the rain water proceeds downwardly through the contact sub-assembly 104, by virtue of the openings provided by perforations 96, the gap 94 between the contact plates 90 and 92 will be bridged at least momentarily by some of the rain water, as illustrated in FIG. 4 at 120. The bridging rain water will complete an electrical circuit between the contact plates 90 and 92 and activate the time delay switching circuit 46 to interrupt the sprinkling cycle in progress. Such activation of the time delay switching circuit 46 will result in the discontinuance of sprinkling for a prescribed timed interval, selected in accordance with the climate conditions at the geographic location of the lawn sprinkling system 10. A timed interval of eight hours has been found satisfactory for most geographic locations. If rainfall is present upon expiration of the timed interval, switch 40 will activate the time delay switching circuit 46 for another prescribed timed interval. However, if the rain has stopped during the timed interval, upon expiration of the timed interval the controller 30 will again operate the lawn sprinkling system 10 in accordance with the prescribed program in the controller 30. It is pointed out that switch 40 is activated immediately upon the onset of rain by virtue of the ability of the switch 40 to receive rain water within the housing 50 and to assure that the rain water reaches and then passes through the contact subassembly 104.

In order to assure operation as set forth above, it is necessary that the switch 40 be sensitive not only to the onset of rain, but to the discontinuance of rain. To that end, the openings provided by the apertures 68, 82 and 84 and the notches 70 in the housing 50, and the perforations 96 in the contact plates 90 and 92, allow relatively free, unimpeded passage of rain water through the switch 40, with immediate activation of the switch 40 upon the onset of rain, and with no accumulation of rain water which could maintain the switch 40 in activated condition after the rain stops. The openings provided in the housing 50 by apertures 68, 82 and 84, and notches 70, preclude essentially the entry of airborne debris into the interior of the housing 50, while enabling relatively free circulation of ambient air through the housing 50, and the contact sub-assembly 104, to evaporate rain water within the housing 50 and return the switch 40 to the inactivated condition. In addition, the relatively free circulation of ambient air enables airflow through the housing 50 in different directions tending to maintain the exterior of the housing 50 free of airborne debris which might otherwise collect on the housing 50 and impede the above-described operation. Thus, the combination of the relatively free passage of rain water through the housing 50, the restricted entry of airborne debris into housing 50, and the relatively free circulation of ambient air through the housing 50 in different directions tends to maintain the switch 40 in optimum operating condition without the necessity for frequent cleaning and maintenance. The conical configuration of the outer surface of top member 54 tends to maintain the top member 54 free of accumulated debris, while assuring that rain water will enter the housing 50 for activation of the switch 40. The conical configuration of the bottom member 56 assures that the rain water which enters the housing 50 will be drained quickly away from the contact sub-assembly 104 so that any rain water which might linger within the housing 50 will not activate the switch 40. The size and placement of the perforations 96 in the contact plates 90 and 92, together with the spacing between the contact plates 90 and 92, assures that rain water will activate the switch 40 as the rain water passes through the contact subassembly 104, and will not accumulate in the contact sub-assembly 104 to maintain that activation after the rain stops. It has been found that perforations 96 having a span SP of about one-sixteenth of an inch, with the perforations 96 of contact plate 90 preferably located in vertical registration with the perforations 96 of contact plate 92, and a gap 94 of about one-sixteenth of an inch will assure the desired immediate activation of the switch 40 in response to the onset of rain and will preclude any accumulation of rain water within the contact subassembly 104, as by surface tension effects or other means, which could maintain activation of the switch 40 after the rain stops. In the illustrated embodiment, perforations 96 are circular and span SP is a diameter of the circular configuration; however, other configurations are feasible.

Figure 2:
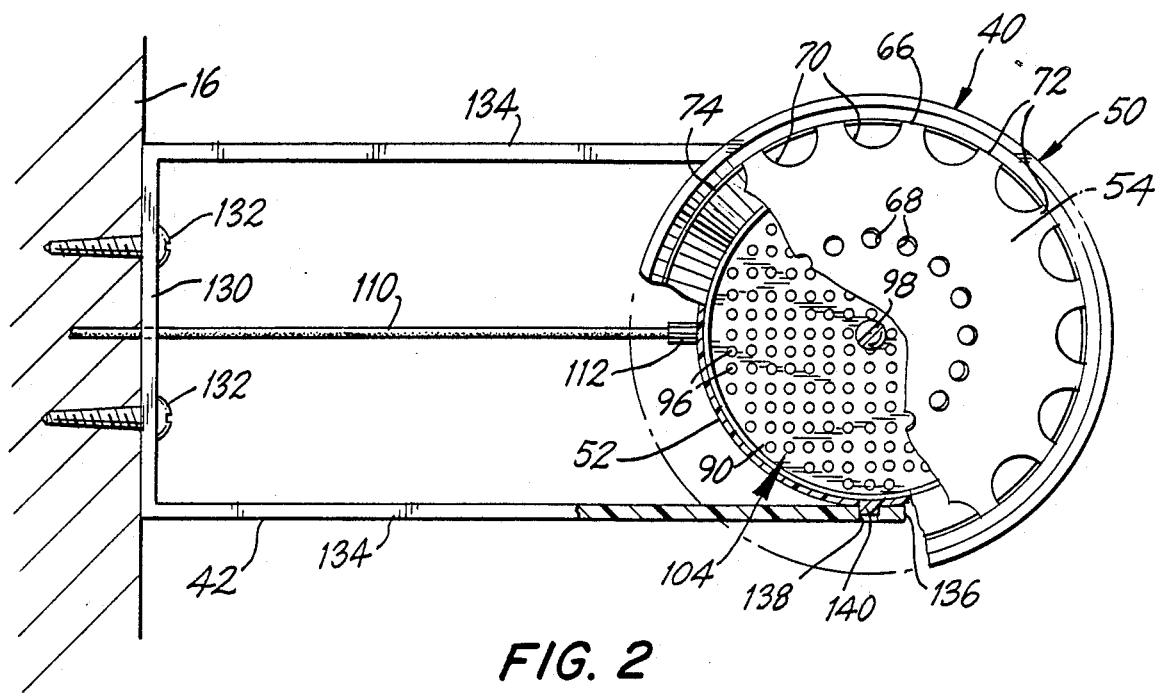
FIG. 2 is an enlarged top plan view of the switch.
Figure 3:
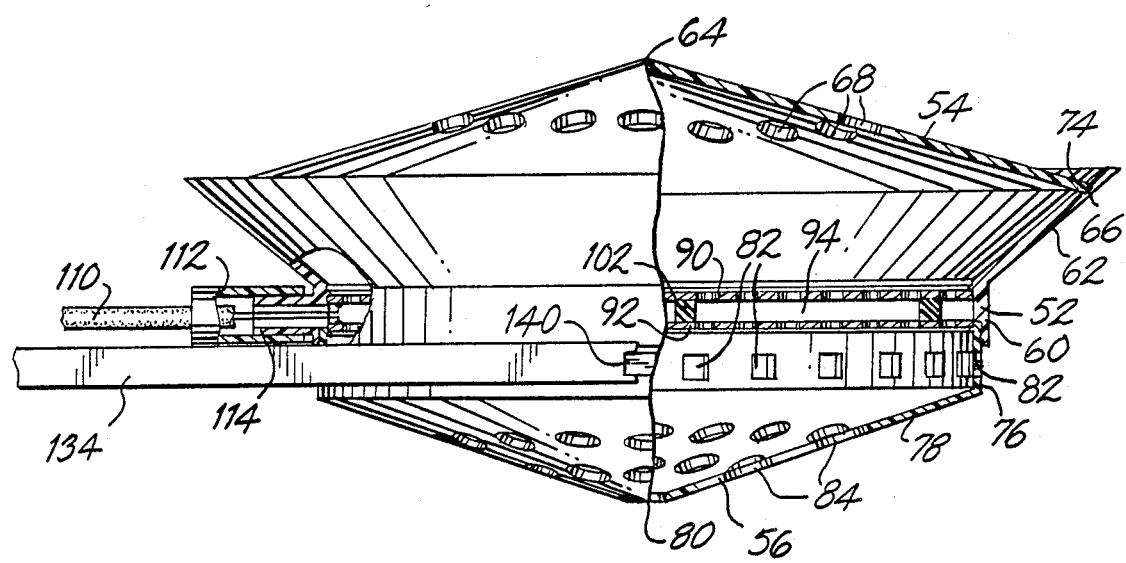
FIG. 3 is a further enlarged, partially sectioned elevational view of the switch.
Figure 6:
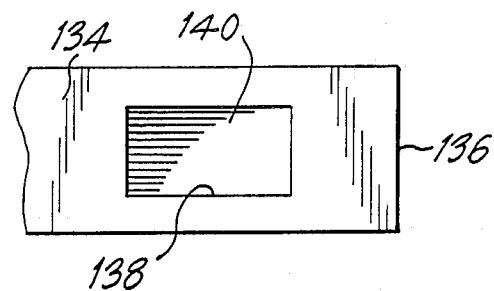
FIG. 6 is an enlarged fragmentary elevational view of a portion of the free end of a bracket arm of the mounting arrangement of the switch construction.

The above-described operation of switch 40 is enhanced further by assuring that the switch 40 is mounted in the most appropriate orientation. That is, it has been found most desirable to maintain the contact sub-assembly 104 oriented so that the contact plates 90 and 92 lie in essentially horizontal planes. In this manner, rain water will tend to pass through the contact sub-assembly 104 and make contact between the spaced apart contact plates 90 and 92, rather than merely run along the contact plates 90 and 92 without necessarily passing between the contact plates 90 and 92. Thus, as seen in FIG. 2, bracket 42 includes a base 130, affixed to the building 16 by means of fasteners 132, and a pair of relatively long arms 134 extending from the base 130 toward free ends 136. A socket 138 is located in each arm 134 adjacent the free end 136 thereof and receives a corresponding projection 140 integral with the housing 50. The projections 140 and the sockets 138 have complementary configurations which enable reception of a projection 140 within a corresponding socket 138 only when the housing 50 is oriented so that the contact sub-assembly 104 is placed in a horizontal orientation. As best seen in FIG. 6, both the projection 140 and the corresponding socket 138 preferably are provided with a rectangular configuration which secures the housing 50 between the arms 134 of the bracket 42 in the preferred orientation. The arms 134 may be deflected resiliently away from one another for selective attachment or detachment of the housing 50.

It will be seen that the above-described construction for switch 40 provides an improvement which attains several objects and advantages, some of which may be summarized as follows: Enables rain water to pass through without substantial accumulation for immediate activation upon the onset of rain and deactivation as soon as the rain stops; allows ambient air to pass through, not only for venting to restore the switch to a deactivated state quickly, but for enabling an omnidirectional flow of air to remove any loose airborne debris which otherwise could impede such deactivation; provides a construction which is highly sensitive to rainfall and remains sensitive over longer service periods without the requirement for frequent maintenance and cleaning to attain long-term sensitivity; exhibits a construction which tends to maintain itself in working order, thereby reducing cleaning and maintenance requirements for long-term reliability; and provides a rugged construction which withstands exposure to ambient conditions for reliable operation over a long service life.

It is to be understood that the above detailed description of a preferred embodiment of the invention is provided by way of example only. Various details of design and construction may be modified without departing from the true spirit and scope of the invention as set forth in the appended claims.

The embodiments of the invention in which an exclusive property or privilege is claimed are defined as follows:

1. A rain water sensitive switch construction for use in connection with irrigation means, such as a lawn sprinkler system, the rain water sensitive switch construction comprising:

a housing having a top and a bottom for installation above ground with the top facing vertically upwardly and the bottom facing vertically downwardly, the top and bottom including openings for allowing rain water to enter the housing and for precluding entry of airborne debris into the housing while enabling relatively free circulation of ambient air through the housing;

first and second electrical contact plates mounted within the housing, between the top and the bottom of the housing, the contact plates being juxtaposed with one another such that the first contact plate overlies the second contact plate with the contact plates spaced apart vertically in close proximity to one another to establish an air gap between the contact plates; and perforations in the first and second contact plates for enabling rain water to pass through the perforations and bridge the gap between the plates as the rain water passes through the perforations, and to enable relatively free circulation of ambient air through the contact plates.

2. The invention of claim 1 wherein the perforations are large enough to preclude effects, such as surface tension, which could impede the passage of the rain water through the contact plates.

3. The invention of claim 2 wherein the perforations have a span of about one-sixteenth of an inch.

4. The invention of claim 1 wherein the air gap is large enough to preclude effects, such as surface tension which could impede the passage of the rain water through the contact plates.

5. The invention of claim 4 wherein the air gap is about one-sixteenth of an inch.

6. The invention of claim 1 wherein the perforations in the first contact plate are registered with corresponding perforations in the second contact plate.

7. The invention of claim 1 wherein the contact plates are essentially planar.

8. The invention of claim 7 wherein the housing includes means for mounting the housing relative to the ground such that the contact plates extend in generally horizontal planes.

9. The invention of claim 1 wherein the contact plates are constructed of stainless steel.

10. The invention of claim 1 wherein the top of the housing has a conical outer configuration with an uppermost apex for resisting the accumulation of airborne debris on the top of the housing.

11. The invention of claim 1 wherein the housing includes means for mounting the housing with the apex of the conical outer configuration uppermost.

* * * * *